(12) United States Patent
Shu

(10) Patent No.: US 12,744,400 B2
(45) Date of Patent: Sep. 22, 2026

(54) CIRCUIT, METHOD, AND OXIMETER FOR INDICATING POWER SUPPLY BY APPLYING DOUBLE-COLOR LIGHT-EMITTING DIODE

(71) Applicant: Guangdong Genial Technology Co., Ltd., Zhaoqing (CN)

(72) Inventor: Chang Shu, Zhaoqing (CN)

(73) Assignee: GUANGDONG GENIAL TECHNOLOGY CO., LTD., Zhaoqing (CN)

( * ) Notice: Subject to any disclaimer, the term of this patent is extended or adjusted under 35 U.S.C. 154(b) by 756 days.

(21) Appl. No.: 18/140,820

(22) Filed: Apr. 28, 2023

(65) Prior Publication Data

US 2024/0146084 A1 May 2, 2024

Related U.S. Application Data

(63) Continuation of application No. PCT/CN2020/124295, filed on Oct. 28, 2020.

(51) Int. Cl.
*H02J 7/82* (2026.01)
*A61B 5/00* (2006.01)
(Continued)

(52) U.S. Cl.
CPC ................ *H02J 7/825* (2026.01); *A61B 5/00* (2013.01); *A61B 5/145* (2013.01); *A61B 5/6826* (2013.01);
(Continued)

(58) Field of Classification Search
CPC ... H02J 7/825; H02J 7/855; H02J 7/80; A61B 5/145; A61B 5/6826; G01R 31/3646
(Continued)

(56) References Cited

U.S. PATENT DOCUMENTS

| | | | | |
|---|---|---|---|---|
| 6,452,363 B1 * | 9/2002 | Jabaji | ........................ | H02J 7/54 320/122 |
| 6,624,350 B2 * | 9/2003 | Nixon | ..................... | H02S 40/38 323/221 |

(Continued)

FOREIGN PATENT DOCUMENTS

| | | |
|---|---|---|
| CN | 203312881 U | 11/2013 |
| CN | 203326671 U | 12/2013 |

(Continued)

OTHER PUBLICATIONS

ÂZacurate 500BL Fingertip Pulse Oximeter Blood Oxygen Saturation Monitor with Batteries Included (Navy Blue), â Zacurate, Amazon.com, First Published for sale Jan. 13, 2017, Accessed Online Mar. 7, https://www.amazon.com/gp/product/B06Y2FFQB9/ref=ask_ql_qh_dp_hza (Year: 2017).*

*Primary Examiner* — John T Trischler
(74) *Attorney, Agent, or Firm* — WPAT, PC

(57) ABSTRACT

A circuit, method, and oximeter for indicating a power supply by applying a double-color light-emitting diode (LED) are provided. The circuit, applied to a finger clip type pulse oximeter, comprises the following components: an MCU module, a double-color LED connected to the MCU module, a voltage measurement module connected to the MCU module, a rechargeable battery module connected to the voltage measurement module, and a power supply input module that is suitable for connection with an external power supply and is connected to the MCU module and the rechargeable battery module, wherein the MCU module is suitable for controlling the double-color LED according to the states of the power supply input module and the rechargeable battery module, so that the finger clip type pulse oximeter presents a visual result directly observable by the human eyes.

11 Claims, 4 Drawing Sheets

(51) Int. Cl.

| | |
|---|---|
| ***A61B 5/145*** | (2006.01) |
| ***G01R 31/36*** | (2020.01) |
| ***H02J 7/00*** | (2006.01) |
| ***H02J 7/80*** | (2026.01) |
| *A61B 5/1455* | (2006.01) |
| *G01R 31/382* | (2019.01) |
| *G08B 5/36* | (2006.01) |
| *H02J 7/63* | (2026.01) |
| *H02J 7/64* | (2026.01) |
| *H02J 7/96* | (2026.01) |

(52) U.S. Cl.
CPC ............ *G01R 31/3646* (2019.01); *H02J 7/80* (2026.01); *H02J 7/855* (2026.01); *A61B 5/14552* (2013.01); *A61B 5/6838* (2013.01); *G01R 31/382* (2019.01); *G08B 5/36* (2013.01); *H02J 7/00* (2013.01); *H02J 7/63* (2026.01); *H02J 7/64* (2026.01); *H02J 7/963* (2026.01)

(58) Field of Classification Search
USPC .......................................................... 320/107
See application file for complete search history.

(56) References Cited

U.S. PATENT DOCUMENTS 6,764,534 B2* 7/2004 McCombs ......... B01D 53/0446 96/111
6,949,133 B2* 9/2005 McCombs ......... B01D 53/0446 96/111
7,498,526 B2* 3/2009 Lohr ...................... B25B 23/18 200/522
8,044,815 B2* 10/2011 Du ...................... G08B 29/181 340/636.12
8,242,751 B2* 8/2012 Yen .......................... H02J 7/02 320/139
8,330,608 B2* 12/2012 Du .......................... G08B 5/36 340/636.12
8,633,674 B2* 1/2014 Law ....................... H02J 7/751 320/112
8,947,040 B2* 2/2015 Law ....................... H02J 7/751 320/112
8,994,827 B2* 3/2015 Mistry ................... G06F 1/163 348/158
9,048,685 B2* 6/2015 Huang ................... H02J 9/065
9,118,059 B2* 8/2015 Kawada ............. H01M 50/209
9,153,994 B2* 10/2015 Wood ...................... H02J 7/485
9,438,049 B2* 9/2016 Xiang ...................... H02J 7/64
9,789,783 B2* 10/2017 Grider ..................... B60L 53/14
9,833,223 B2* 12/2017 Wood ...................... H02J 7/485
9,962,082 B2* 5/2018 Kim ...................... G16H 50/20
10,008,871 B2* 6/2018 Xiang ..................... H02J 7/485
10,031,587 B2* 7/2018 Heo .................. A61B 5/14551
10,185,416 B2* 1/2019 Mistry ................. G06F 3/0346
10,194,060 B2* 1/2019 Mistry ................... G06F 3/017
10,216,677 B2* 2/2019 Jung .................. G06F 13/4282
10,278,681 B2* 5/2019 Wood ...................... H02J 7/485
10,492,984 B2* 12/2019 Marton ............. A61H 23/0254
10,516,291 B2* 12/2019 Kent ......................... G06F 1/28
10,561,574 B1* 2/2020 Marton ................ A61H 23/006
10,569,084 B2* 2/2020 McGeoch ............ A61N 1/0408
10,729,177 B2* 8/2020 Dendy .................... A24F 40/50
10,750,779 B2* 8/2020 Schennum ............. H02J 7/825
10,888,492 B2* 1/2021 Marton ................ A61H 23/006
10,905,627 B2* 2/2021 Marton ............. A61H 23/0254
10,912,708 B2* 2/2021 Marton ............. A61H 23/0254
10,918,289 B1* 2/2021 Wasson ................ A61B 5/0022
10,970,674 B2* 4/2021 Hicks .................... G07F 7/0886
10,971,938 B2* 4/2021 Park ..................... A61B 5/6898
11,237,719 B2* 2/2022 Mistry ................. G06F 3/0488
11,240,408 B2* 2/2022 Mistry ................... G06F 3/014
11,432,774 B2* 9/2022 Heo ....................... H10K 39/32
11,456,503 B2* 9/2022 Shivaraju ............. H01M 10/48
11,462,926 B2* 10/2022 Schennum ............. H02J 7/825
11,641,882 B2* 5/2023 Dendy .................... A24F 40/50 392/404
11,764,701 B2* 9/2023 Richards .......... H02M 3/33523 307/31
11,894,707 B1* 2/2024 Olsson .................... H02J 7/751
11,901,527 B2* 2/2024 Chartier ............. H01M 10/488
11,903,700 B2* 2/2024 Marriott ................. H05B 45/10
11,978,869 B2* 5/2024 Chartier ............. H01M 10/488
11,998,304 B2* 6/2024 Wasson ............. A61B 5/14535
12,042,282 B2* 7/2024 Fernando .......... A61B 5/14552
12,235,679 B2* 2/2025 von Badinski ......... G06F 1/163
12,244,241 B2* 3/2025 Richards .......... H02M 3/33523
12,362,578 B2* 7/2025 Schennum ............. H02J 7/825
12,443,338 B2* 10/2025 Mistry .................. G06F 3/0488
12,465,214 B2* 11/2025 Stump .................... A61B 5/318
12,530,050 B2* 1/2026 von Badinski ......... G06F 1/163
12,551,167 B2* 2/2026 Kangas ................ A61B 5/7221
2002/0108648 A1* 8/2002 Nixon ..................... H02S 40/38 136/291
2003/0167924 A1* 9/2003 McCombs .......... B01D 53/053 96/111
2004/0149133 A1* 8/2004 McCombs ............. A61P 11/00 96/111
2005/0187442 A1* 8/2005 Cho ..................... A61B 5/7475 374/E13.002
2007/0205908 A1* 9/2007 Du .......................... G08B 5/36 340/815.45
2007/0256914 A1* 11/2007 Lohr ...................... B25B 23/18 200/5 A
2010/0277119 A1* 11/2010 Montague ................. H02J 7/70 600/301
2011/0163719 A1* 7/2011 Law ....................... H02J 7/751 320/110
2011/0211325 A1* 9/2011 Kawada ............. H01M 50/209 361/807
2011/0316473 A1* 12/2011 Yen .......................... H02J 7/02 320/128
2012/0038483 A1* 2/2012 Du .......................... G08B 5/36 340/636.1
2013/0096539 A1* 4/2013 Wood ...................... H02J 7/485 606/1
2013/0187470 A1 7/2013 Huang
2014/0097796 A1* 4/2014 Law ....................... H02J 7/751 320/113
2014/0139454 A1* 5/2014 Mistry ................... G06F 3/017 345/173
2014/0139637 A1* 5/2014 Mistry .................. H04N 23/51 348/46
2014/0143784 A1* 5/2014 Mistry ................. G06F 3/0488 718/102
2014/0194712 A1* 7/2014 Hu ..................... A61B 5/14552 600/340
2015/0015187 A1* 1/2015 Xiang ...................... H02J 7/64 320/162
2015/0181087 A1* 6/2015 Mistry ................... G06F 3/017 348/158
2015/0297079 A1* 10/2015 Tateda ................ A61B 5/0015 600/340
2016/0051238 A1* 2/2016 Wood ...................... H02J 7/485 606/1
2016/0085331 A1* 3/2016 Kubo .................... G16H 20/30 345/173
2016/0109959 A1* 4/2016 Heo ..................... A61B 5/6898 340/5.52
2016/0226286 A1* 8/2016 Xiang ..................... H02J 7/485
2016/0367138 A1* 12/2016 Kim ..................... A61B 5/6898
2017/0013876 A1* 1/2017 Schennum ............. H02J 7/825
2017/0185557 A1* 6/2017 Jung .................. G06F 13/4282
2017/0223807 A1* 8/2017 Recker ...................... H02J 9/02
2017/0267117 A1* 9/2017 Grider ..................... B60L 53/14
2017/0304618 A1* 10/2017 Mcgeoch .......... A61N 1/36014
2017/0347995 A9* 12/2017 Wood ...................... H02J 7/485
2018/0000469 A1* 1/2018 Wood ...................... H02J 7/485
2018/0027878 A1* 2/2018 Dendy .................... A24F 40/50
2018/0212449 A1* 7/2018 Park ..................... A61B 5/6898
2018/0316211 A1* 11/2018 Kent ......................... G06F 1/30

(56) References Cited

U.S. PATENT DOCUMENTS

2019/0166285 A1* 5/2019 Mistry .................... G06F 3/014
2019/0228374 A1* 7/2019 Hicks ................... G06Q 20/204
2019/0239821 A1* 8/2019 Heo ................... A61B 5/14551
2019/0254921 A1* 8/2019 Marton ................ A61H 23/006
2019/0254922 A1* 8/2019 Marton ................ A61H 23/006
2020/0046601 A1* 2/2020 Marton .............. A61H 23/0254
2020/0253818 A1* 8/2020 Marton ................ A61H 23/006
2020/0337381 A1* 10/2020 Dendy .................... A24F 40/50
2020/0345064 A1* 11/2020 Schennum .............. H02J 7/825
2020/0352823 A1* 11/2020 Marton ................ A61H 23/006
2021/0059586 A1* 3/2021 Marriott ............... A61B 5/7225
2021/0169345 A1* 6/2021 Wasson .............. G01N 21/3577
2021/0234140 A1* 7/2021 Shivaraju .............. H01M 10/48
2021/0351716 A1* 11/2021 Richards ........... H02M 3/33523
2021/0361524 A1* 11/2021 Marton ................ A61H 23/006
2022/0021040 A1* 1/2022 Chartier .............. H01M 10/488
2022/0021062 A1* 1/2022 Chartier .............. H01M 10/488
2022/0121339 A1* 4/2022 Mistry .................. G06F 3/0488
2022/0407326 A1* 12/2022 Schennum .............. H02J 7/825
2023/0080370 A1* 3/2023 Katz .................. A61H 23/0254
601/101
2023/0188052 A1* 6/2023 Richards ........... H02M 3/33523
307/31
2023/0190100 A1* 6/2023 Stump .................... A61B 5/746
600/301
2023/0200690 A1* 6/2023 Haga .................. A61B 5/02433
600/300
2023/0240372 A1* 8/2023 Dendy .................... A24F 40/50
392/404
2023/0240567 A1* 8/2023 Kitamura ........... A61B 5/14552
600/323
2023/0363670 A1* 11/2023 Fernando ........... A61B 5/14552
2024/0007017 A1* 1/2024 Richards ........... H02M 3/33523
2024/0122548 A1* 4/2024 Kangas ................ A61B 5/7221
2024/0126329 A1* 4/2024 Von Badinski ......... G06F 1/163
2024/0324916 A1* 10/2024 Fernando ........... A61B 5/14552
2024/0419125 A1* 12/2024 Kim ....................... G04G 17/04
2025/0321618 A1* 10/2025 von Badinksi ......... G06F 1/163
2026/0003495 A1* 1/2026 Mistry .................. G06F 3/0488

FOREIGN PATENT DOCUMENTS

CN 203504217 U 3/2014
CN 105356554 A 2/2016
CN 206471881 U 9/2017
CN 211698114 U 10/2020

* cited by examiner

CIRCUIT, METHOD, AND OXIMETER FOR INDICATING POWER SUPPLY BY APPLYING DOUBLE-COLOR LIGHT-EMITTING DIODE

TECHNICAL FIELD

The present invention relates to a circuit, method, and oximeter for indicating a power supply by applying a double-color light-emitting diode (LED).

BACKGROUND

The existing finger clip type pulse oximeters are mainly powered by AAA7 batteries, and cannot be powered by lithium batteries and the like; besides, when the battery level, represented by an energy bar, is low, a prompt that the LCD screen flashes or the energy bar is empty is usually given.

However, since the LCD screen of the finger clip type pulse oximeter is generally about 1 inch in size, the display icon for the energy bar is small; moreover, different from using a mobile phone, a user, when using a finger clip type pulse oximeter, generally does not pay close attention to the battery level, and may not know that there is no electricity only until the battery is completely dead or the finger clip type pulse oximeter cannot be turned on, unless there is a more intuitive way to observe.

Therefore, the existing finger clip type pulse oximeters have the following disadvantages:

(1) Displaying the low battery level through the flashing of the LCD screen is easy to cause trouble for a user and interfere with viewing the test data;

(2) although the energy bar can display the battery level, a user tends to neglect the display here when using the oximeter, such that the user may not know the battery is dead only until the oximeter is shut down automatically; and (3) failure to support the online charging function may cause the oximeter to become unusable because the battery is not replaced in time, and especially may also increase a user's psychological pressure of using the oximeter if there is no spare battery at home.

SUMMARY

A first object of the present invention is to provide a circuit for indicating a power supply by applying a double-color LED, this circuit enabling a user to more intuitively know the battery level of the finger clip type pulse oximeter through the double-color LED.

A second object of the present invention is to provide a method for indicating a power supply by applying the above circuit, this method enabling a user to more intuitively know the battery level of the finger clip type pulse oximeter.

A third object of the present invention is to provide an oximeter for indicating a power supply by applying a double-color LED, this oximeter enabling a user to more intuitively know its battery level.

For the above-mentioned first object, the present invention adopts following technical solution:

A circuit, applied to a finger clip type pulse oximeter, for indicating a power supply by applying a double-color LED is provided, comprising the following components:

an MCU module U1;

a double-color LED module, including a double-color LED D1 and connected to the MCU module U1;

a voltage measurement module connected to the MCU module U1;

a rechargeable battery module connected to the voltage measurement module; and a power supply input module, which is suitable for connection with an external power supply and is connected to the MCU module U1 and the rechargeable battery module;

wherein the MCU module U1 is suitable for controlling the double-color LED D1 according to the states of the power supply input module and the rechargeable battery module, so that the finger clip type pulse oximeter presents a visual result directly observable by the human eyes.

Furthermore, with the power supply input module including a socket U2, a fuse F2 is connected between the socket U2 and the output terminal of the power supply input module; the output terminal of the power supply input module is connected to the rechargeable battery module, and connected to the MCU module U1 through an insertion detection module.

Furthermore, the insertion detection module includes a resistor R1, which has one terminal connected to the MCU module U1 and the other terminal connected to the output terminal of the power supply input module.

Furthermore, the rechargeable battery module comprises a lithium battery BAT1, and a charging management chip U3 connected to the output terminal of the power supply input module; the lithium battery BAT1, with its negative electrode grounded, has its positive electrode connected to the charging management chip U3 and connected to the MCU module U1 through the voltage measurement module.

Furthermore, the voltage measurement module includes resistors R7 and R8, one terminal of the resistor R7 being connected to the positive electrode of the lithium battery BAT1; the resistor R8 has its one terminal grounded, and the other terminal connected to the other terminal of the resistor R7 and then connected to the MCU module U1.

Furthermore, the double-color LED D1 comprises a first LED capable of exhibiting a first color, and a second LED capable of exhibiting a second color, with the first color different from the second color; the double-color LED module further comprises resistors R4 and R5; the anode of the first LED is connected to a VDD pin of the MCU module U1 through the resistor R4, and the anode of the second LED is connected to the same VDD pin of the MCU module U1 through the resistor R5; the cathode of the first LED is directly connected to one I/O pin of the MCU module U1, and the cathode of the second LED is directly connected to the other I/O pin of the MCU module U1.

Furthermore, the above description that "the finger clip type pulse oximeter presents a visual result directly observable by the human eyes" is specifically as follows:

When the power supply input module is connected to the external power supply, and the lithium battery BAT1 is being charged, the MCU module U1 controls the first LED to flash in the first color at a predetermined frequency;

when the power supply input module is connected to the external power supply, and the lithium battery BAT1 is fully charged, the MCU module U1 controls the first LED to be always on in the first color;

when the power supply input module is not connected to the external power supply, and the MCU module U1 detects that the voltage of the detection terminal of the voltage measurement module is lower than a first predetermined voltage, the MCU module U1 controls the second LED to be always on in the second color; and when the power supply input module is not connected to the external power supply, and the MCU module U1 detects that the voltage of the detection terminal of the voltage measurement module is lower than a second predetermined voltage, the MCU module U1 controls the second LED to flash in the second color at a predetermined frequency;

wherein the second predetermined voltage is lower than the first predetermined voltage.

Furthermore, the charging management chip has a VIN pin connected to the power supply input module, a BAT pin connected to the lithium battery BAT1 for charging current output, and a CHG pin connected to an indication LED D2 for charging state output, the indication LED D2 capable of exhibiting a third color.

For the above-mentioned second object, the present invention adopts following technical solution:

When the power supply input module is connected to the external power supply, and the lithium battery BAT1 of the rechargeable battery module is being charged, the MCU module U1 controls the first LED of the double-color LED D1 to flash in the first color at a predetermined frequency;

when the power supply input module is connected to the external power supply, and the lithium battery BAT1 of the rechargeable battery module is fully charged, the MCU module U1 controls the first LED of the double-color LED D1 to be always on in the first color;

when the power supply input module is not connected to the external power supply, and the MCU module U1 detects that the voltage of the detection terminal of the voltage measurement module is lower than a first predetermined voltage, the MCU module U1 controls the second LED of the double-color LED D1 to be always on in the second color; and when the power supply input module is not connected to the external power supply, and the MCU module U1 detects that the voltage of the detection terminal of the voltage measurement module is lower than a second predetermined voltage, the MCU module U1 controls the second LED of the double-color LED D1 to flash in the second color at a predetermined frequency;

wherein the second predetermined voltage is lower than the first predetermined voltage.

For the above-mentioned third object, the present invention adopts following technical solution:

An oximeter, being of a finger clip type pulse oximeter, for indicating a power supply by applying a double-color LED is provided, comprising a body and the above-mentioned circuit; the body is provided on the surface with a display screen and an indication position located on one side of the display screen, with the double-color LED D1 set corresponding to the indication position.

The present invention has the following beneficial effects: The double-color LED is configured for the finger clip type pulse oximeter having a small display screen, so that two colors of light can be emitted by the double-color LED and can be controlled through the power supply input module and the rechargeable battery module, enabling the finger clip type pulse oximeter to present a visual result directly observable by the human eyes; in this way, through the intuitive lighting display of the LED, a user can visually check the battery level, thereby eliminating the user's psychological pressure of being unable to use the oximeter due to a low battery level.

DETAILED DESCRIPTION OF EMBODIMENTS

In order to facilitate a better understanding of the objects, structures, features and effects of the present invention, the present invention will now be further described with reference to the accompanying drawings and specific embodiments.

An example of the present invention provides an oximeter for indicating a power supply by applying a double-color LED, with the oximeter being of a finger clip type pulse oximeter.

Figure 1:
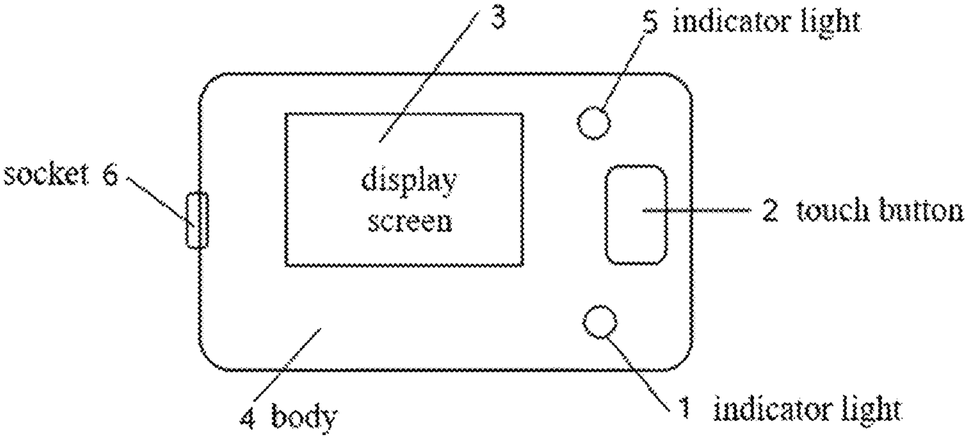
FIG. 1 schematically shows the structure of a finger clip type pulse oximeter according to an example of the present invention.

As shown in FIG. 1, the oximeter comprises a body 4 and a circuit, the circuit being arranged in the body 4 and including a rechargeable lithium battery; the body 4 is provided on the surface with a display screen 3, on one side of which is arranged a touch button 2 and two spaced indication positions; indicator lights 1 and 5 are respectively arranged at the two indication positions, wherein the indicator light 5 is a double-color LED for indicating the power supply, and the indicator light 1 is used for indicating other states; on the other side of the display screen is further arranged a socket 6 suitable for charging access, which is, in an example, a USB socket connected to an external power supply through a charging cable for charging the lithium battery.

Figure 2:
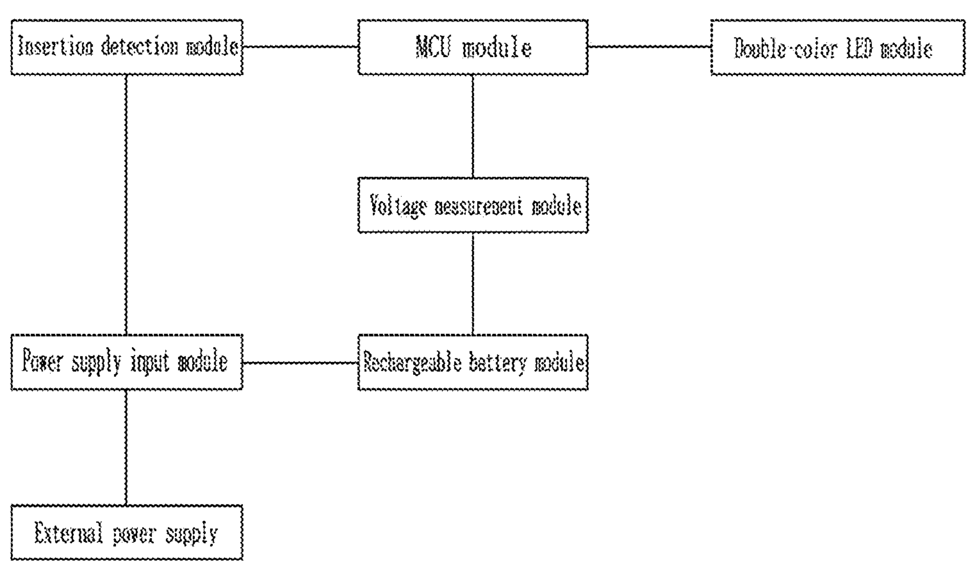
FIG. 2 is a block diagram showing the circuit structure of a finger clip type pulse oximeter according to an example of the present invention.

The circuit therein uses a double-color LED to indicate the power supply. As shown in FIG. 2, the circuit comprises an MCU module, a double-color LED module connected to the MCU module, a voltage measurement module connected to the MCU module, a rechargeable battery module connected to the voltage measurement module, and a power supply input module that is suitable for connection with an external power supply and is connected to the MCU module and the rechargeable battery module.

Figure 3:
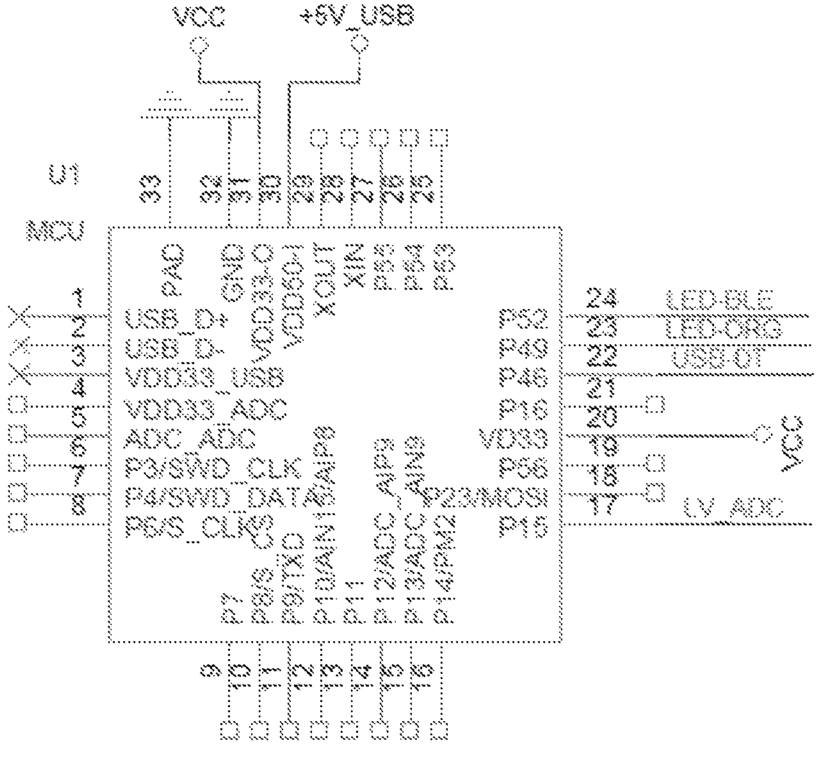
FIG. 3 shows the circuit structure of an MCU module according to an example of the present invention.

An MCU (i.e. micro-control unit) module of any suitable model, e.g. STM32L071CB, can be used in the present invention. In an example, the pin structure and circuit connection relationship of the MCU module U1 are shown in FIG. 3.

Figure 8:
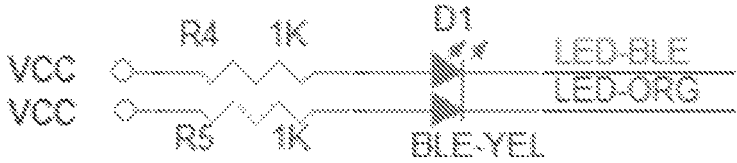
FIG. 8 shows the circuit structure of a double-color LED module according to an example of the present invention.

As shown in FIG. 8, the double-color LED module comprises a double-color LED D1, a resistor R4, and a resistor R5; the double-color LED D1 comprises a first LED capable of exhibiting a first color, and a second LED capable of exhibiting a second color, with the first color different from the second color. The first and second colors may be any different colors; for example, in an example, the first color is blue and the second color is orange. The anode of the first LED is connected to the MCU module U1 through the resistor R4, and the anode of the second LED is connected to the MCU module U1 through the resistor R5. In an example, the resistors R4 and R5 each have a resistance of 1 kΩ. The cathode of the first LED is directly connected to one I/O pin P52 of the MCU module U1, and the cathode of the second LED is directly connected to the other I/O pin P49 of the MCU module U1.

The MCU module U1 is suitable for controlling the double-color LED according to the states of the power supply input module and the rechargeable battery module, so that the finger clip type pulse oximeter presents a visual result directly observable by the human eyes.

Figure 5:
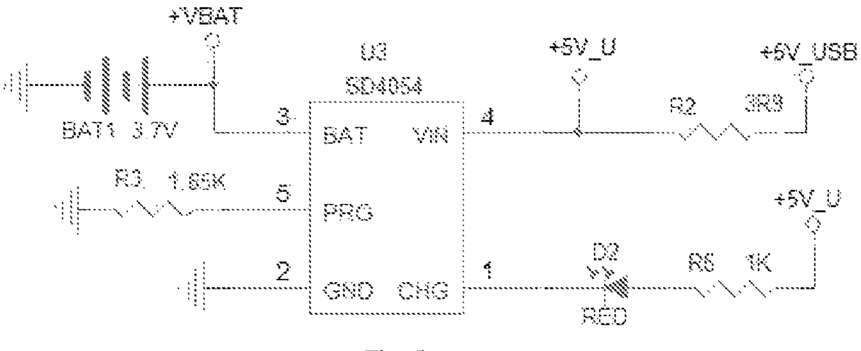
FIG. 5 shows the circuit structure of a rechargeable battery module according to an example of the present invention.

As shown in FIG. 5, the rechargeable battery module comprises a lithium battery BAT1, and a charging management chip U3 connected to the output terminal +5V_USB of the power supply input module; the lithium battery BAT1, with its negative electrode grounded, has its positive electrode +VBAT connected to the charging management chip U3 and connected to pin P15 of the MCU module U1 through the voltage measurement module. The charging management chip may be of any suitable model, e.g. SD4054. In an example, the charging management chip U3 has a VIN pin connected to the power supply input module, a BAT pin connected to the lithium battery BAT1 for charging current output, a PRG pin for charging current setting, charging current monitoring and shutdown, a GND pin for grounding, and a CHG pin for charging state output. The CHG pin is connected to an indication LED D2, which is capable of exhibiting a third color. The third color may be different from both the first color and the second color, for example, the third color may be yellow. The indication LED D2 is used to detect the working state of the charging management chip. In some examples, as shown in FIG. 1, the indication LED D2 can be correspondingly arranged at the other indication position of the body 4; that is, one indicator light 5 on the surface of the body 4 is a double-color LED D1, and the other indicator light 1 is an indication LED D1. In this way, whether the charging management chip U3 is working normally can be judged by directly observing the indication LED D2 with the human eyes.

Figure 4:
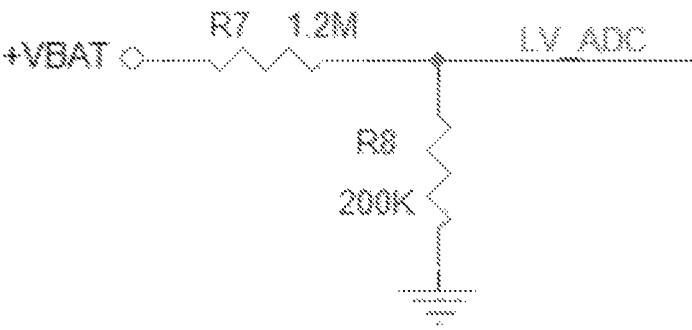
FIG. 4 shows the circuit structure of a voltage measurement module according to an example of the present invention.

As shown in FIG. 4, the voltage measurement module includes resistors R7 and R8, one terminal of the resistor R7 being connected to the positive electrode +VBAT of the lithium battery BAT1; one terminal of the resistor R8 is grounded, and the other terminal is connected to the other terminal of the resistor R7 to form a detection terminal LV_ADC, which is connected to pin P15 of the MCU module U1. In an example, the resistance of R7 is 1.2 MΩ, and the resistance of R8 is 200 KΩ. The function of the voltage measurement module is to divide the voltage, i.e. to divide the voltage through the resistors R7 and R8, so as to avoid the direct measurement of the voltage of the positive electrode +VBAT of the lithium battery BAT1, thereby preventing the voltage of the positive electrode +VBAT of the lithium battery BAT1 from being too high for measurement.

Figure 6:
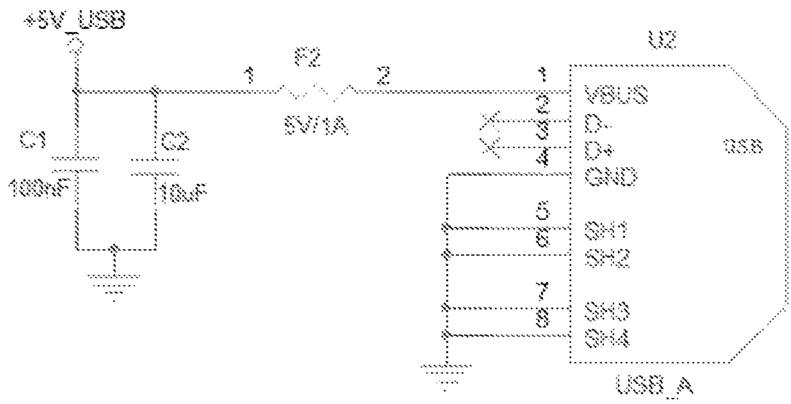
FIG. 6 shows the circuit structure of a power supply input module according to an example of the present invention.

As shown in FIG. 6, the power supply input module includes a socket U2, which, in an example, is a USB socket; with the external power supply being a charging adapter, the socket U2 can be connected to the charging adapter through a charging cable. As shown in FIG. 1, the socket U2 corresponds to the socket 6 arranged on the body 4. A fuse F2 is connected between the socket U2 and the output terminal +5V_USB of the power supply input module. In an example, the fuse F2 has a rated voltage of 5 V and a rated current of 1 A. The output terminal +5V_USB of the power supply input module is connected to the VIN pin of the rechargeable battery module through a resistor R2, which, in one example, has a resistance of 3.9Ω.

Figure 7:
FIG. 7 shows the circuit structure of an insertion detection module according to an example of the present invention.

As shown in FIG. 3, the output terminal +5V_USB of the power supply input module is directly connected to pin VDD50-I of the MCU module U1 to supply power to the MCU module U1. In addition, as shown in FIG. 7, the output terminal +5V_USB of the power supply input module is also connected to pin P46 of the MCU module U1 through the insertion detection module, so that the MCU module U1 can detect whether the power supply input module is connected to the external power supply. The power supply input module also includes capacitors C1 and C2. One terminal of the capacitor C1 is grounded, and the other terminal is connected to the output terminal +5V_USB; one terminal of the capacitor C2 is grounded, and the other terminal is connected to the output terminal +5V_USB. That is, the capacitors C1 and C2 are connected in parallel. In an example, the capacitance of the capacitor C1 is 100 nF, and the capacitance of the capacitor C2 is 10 μF.

As shown in FIG. 7, the insertion detection module includes a resistor R1, which has one terminal USB-DT connected to pin P46 of the MCU module U1 and the other terminal +5V_USB connected to the output terminal +5V_USB of the power supply input module; the resistor R1, as a pull-up current-limiting resistor, is used for +5V_USB to provide an input high-level signal to the I/O pin of the MCU module U1 through the resistor R1, so that the MCU module U1 can accurately detect the high level of 5 V.

According to the above circuit, the present invention provides the following method for indicating the power supply, so that the finger clip type pulse oximeter presents a visual result directly observable by the human eyes, and a user can more intuitively understand the power supply state of the finger clip type pulse oximeter.

The method for indicating the power supply comprises the following situations: When the socket U2 of the power supply input module is connected to the external power supply through the charging cable, the charging power supply reaches the network +5V_USB through the fuse F2, the +5V_USB power supply enters the MCU module U1 through the network USB-DT via the resistor R1, and pin P46 of the MCU module U1 will automatically detect that there is a high level of 5V, so it is considered that an external charging power supply is connected at this time;

- if pin P15 of the MCU module U1 detects that the lithium battery BAT1 is in a charging state through the detection of the detection terminal LV_ADC, the MCU module U1 will send a pulse control signal of a certain frequency through pin P52, so that the first LED flashes in the first color (e.g. blue) at a predetermined frequency;
- if pin P15 of the MCU module U1 detects that the lithium battery BAT1 is fully charged through the detection of the detection terminal LV_ADC when the external power supply is connected, the MCU module U1 will send a low-level signal through pin P52 to directly light the first LED, so that the first LED is always on in the first color (e.g. blue);
- when the socket U2 of the power supply input module is not connected to the external power supply, pin P15 of the MCU module U1 will automatically detect the level of the network LV_ADC as soon as the finger clip type pulse oximeter is turned on; when the LV_ADC is in a low-voltage state identified by the program control algorithm (that is, the voltage of the detection terminal LV_ADC of the voltage measurement module is lower than a first predetermined voltage), it indicates that the lithium battery BAT1 starts to run low; at this time, the MCU module U1 will send a low-level signal through pin P49 to directly light the second LED, so that the second LED is always on in the second color (e.g. orange), thereby prompting the user to charge as soon as possible; and when the detection terminal LV_ADC is in an extremely low-voltage state identified by the program control algorithm (that is, the voltage of the detection terminal LV_ADC of the voltage measurement module is lower than a second predetermined voltage, with the second predetermined voltage lower than the first predetermined voltage), it indicates that the lithium battery BAT1 runs seriously low; at this time, the MCU module U1 will send a pulse control signal of a certain frequency through pin P49, so that the second LED flashes in the second color (e.g. orange) at the predetermined frequency, thereby prompting the user that the oximeter is about to shut down automatically and please charge it immediately.

The above detailed description is only the description of the preferred examples of the present invention, and is not intended to limit the patent scope of the present invention. Therefore, all equivalent technical changes made by using the content of the present invention are included in the patent scope of the present invention.

The invention claimed is:

1. A circuit, applied to a finger clip type pulse oximeter, for indicating a power supply by applying a double-color light-emitting diode (LED), characterized in that the circuit comprises:

a micro-controller unit (MCU) module;

a double-color LED module, including a double-color LED and connected to the MCU module;

a voltage measurement module connected to the MCU module;

a rechargeable battery module connected to the voltage measurement module; and a power supply input module, which is suitable for connection with an external power supply and is connected to the MCU module and the rechargeable battery module;

wherein the MCU module is suitable for controlling the double-color LED according to the states of the power supply input module and the rechargeable battery module, so that the finger clip type pulse oximeter presents a visual result directly observable by the human eyes;

wherein the power supply input module comprises a socket and a fuse, and the fuse is connected to the socket;

wherein the circuit further comprises an insertion detection module, and the power supply input module is connected to the MCU module through the insertion detection module; and wherein the insertion detection module comprises a first resistor, and the first resistor is directly connected between an input/output (I/O) pin of the MCU module and the fuse.

2. An oximeter for indicating a power supply by applying a double-color LED, characterized in that: the oximeter, being of a finger clip type pulse oximeter, comprises a body and the circuit according to claim 1; the body is provided on a surface with a display screen and an indication position located on one side of the display screen, with the double-color LED set corresponding to the indication position.

3. The circuit for indicating a power supply by applying a double-color LED according to claim 1, wherein the power supply input module further comprises a first capacitor and a second capacitor, and the first capacitor and the second capacitor are connected in parallel; and one terminal of each of the first capacitor and second capacitor is grounded, and the other terminal of each of the first capacitor and the second capacitor is connected to an output terminal of the power supply input module.

4. The circuit for indicating a power supply by applying a double-color LED according to claim 3, wherein a capacitance of the first capacitor is 100 nano farads (nF), and a capacitance of the second capacitor is 10 micro farads (μF).

5. The circuit for indicating a power supply by applying a double-color LED according to claim 1, characterized in that: the rechargeable battery module comprises a lithium battery, and a charging management chip connected to an output terminal of the power supply input module; the lithium battery, with its negative electrode grounded, has its positive electrode connected to the charging management chip and connected to the MCU module through the voltage measurement module.

6. The circuit for indicating a power supply by applying a double-color LED according to claim 5, characterized in that: the charging management chip has a VIN pin connected to the power supply input module, a battery (BAT) pin connected to the lithium battery for charging current output, and a charging (CHG) pin connected to an indication LED for charging state output, the indication LED capable of exhibiting a third color.

7. The circuit for indicating a power supply by applying a double-color LED according to claim 4, characterized in that: the voltage measurement module comprises a second resistor and a third resistor, one terminal of the second resistor being connected to the positive electrode of the lithium battery; the third resistor has its one terminal grounded, and the other terminal connected to the other terminal of the second resistor and then connected to the MCU module.

8. The circuit for indicating a power supply by applying a double-color LED according to claim 7, wherein the second resistor has a resistance of 1.2 megaohms (MΩ) and the third resistor has a resistance of 200 kiloohms (KΩ).

9. The circuit for indicating a power supply by applying a double-color LED according to claim 4, characterized in that: the double-color LED D1 comprises a first LED capable of exhibiting a first color, and a second LED capable of exhibiting a second color, with the first color different from the second color; the double-color LED module further comprises a fourth resistor and a fifth resistor; an anode of the first LED is connected to a voltage drain supply (VDD) pin of the MCU module through the fourth resistor, and an anode of the second LED is connected to the same VDD pin of the MCU module through the fifth resistor; a cathode of the first LED is directly connected to one I/O pin of the MCU module, and a cathode of the second LED is directly connected to the other I/O pin of the MCU module.

10. The circuit for indicating a power supply by applying a double-color LED according to claim 9, characterized in that:

the above description that the finger clip type pulse oximeter presents a visual result directly observable by the human eyes is specifically as follows:

when the power supply input module is connected to the external power supply, and the lithium battery is being charged, the MCU module controls the first LED to flash in the first color at a predetermined frequency;

when the power supply input module is connected to the external power supply, and the lithium battery is fully charged, the MCU module controls the first LED to be always on in the first color;

when the power supply input module is not connected to the external power supply, and the MCU module detects that the voltage of the detection terminal of the voltage measurement module is lower than a first predetermined voltage, the MCU module controls the second LED to be always on in the second color; and when the power supply input module is not connected to the external power supply, and the MCU module detects that the voltage of the detection terminal of the voltage measurement module is lower than a second predetermined voltage, the MCU module controls the second LED to flash in the second color at a predetermined frequency;

wherein the second predetermined voltage is lower than the first predetermined voltage.

11. A method, applied to a finger clip type pulse oximeter, for indicating a power supply by applying the circuit according to claim 1, characterized in that the method is specifically as follows:

when the power supply input module is connected to the external power supply, and the lithium battery of the rechargeable battery module is being charged, the MCU module controls the first LED of the double-color LED to flash in the first color at a predetermined frequency;

when the power supply input module is connected to the external power supply, and the lithium battery of the rechargeable battery module is fully charged, the MCU module controls a first LED of the double-color LED to be always on in a first color;

when the power supply input module is not connected to the external power supply, and the MCU module detects that a voltage of a detection terminal of the voltage measurement module is lower than a first predetermined voltage, the MCU module controls a second LED of the double-color LED to be always on in a second color; and when the power supply input module is not connected to the external power supply, and the MCU module detects that the voltage of the detection terminal of the voltage measurement module is lower than a second predetermined voltage, the MCU module controls the second LED of the double-color LED to flash in the second color at a predetermined frequency;

wherein the second predetermined voltage is lower than the first predetermined voltage.

* * * * *